US00PP15100P2

(12) United States Plant Patent
van Straalen et al.

(10) Patent No.: US PP15,100 P2
(45) Date of Patent: Aug. 24, 2004

(54) ASTER PLANT NAMED 'DUKASTER'

(50) Latin Name: *Aster novi-belgii L.*
Varietal Denomination: Dukaster

(75) Inventors: Harry W. M. van Straalen, Rijsenhout (NL); Wilfried J. Poland, Wervershoof (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 10/426,848

(22) Filed: May 1, 2003

(51) Int. Cl.[7] ..... A01H 5/00
(52) U.S. Cl. ..... Plt./355
(58) Field of Search ..... Plt./355

*Primary Examiner*—Bruce R. Campell
*Assistant Examiner*—Michelle Kizilkaya
(74) *Attorney, Agent, or Firm*—Parkhurst & Wendel, L.L.P.

(57) ABSTRACT

An Aster plant named 'Dukaster' characterized by its medium sized blooms with pink ray-florets and yellow disc florets, which can be propagated by means of cuttings from cuttings and produced with a short period.

3 Drawing Sheets

Scientific name: *Aster novi-belgii* L. 'Dukaster'.

RELATED CULTIVARS

'Dukaster' is related to 'Dynaster' (copending U.S. Plant patent application Ser. No. 10/426,849 filed May 1, 2003) and 'Diamaster' (copending U.S. Plant patent application Ser. No. 10/426,847 filed May 1, 2003), which are all aster varieties developed from similar breeding programs.

BACKGROUND OF THE INVENTION

'Dukaster' is a product of a breeding-program that had the objective of creating new Aster cultivars, which can be grown as pot plants and propagated by means of cuttings from cuttings, similar to the cultivation and propagation of all year round chrysanthemum. The new plant of the present invention comprises a new and distinct cultivar of an Aster plant. 'Dukaster' is a seedling from a cross in a breeding program maintained under the control of inventor. The female parent is an unnamed seedling not available to inventor for description. The male parent is unknown, being a mixed population of a group of male parents. To the knowledge of the inventors, both the female parent and the male parent are unpatented. The new and distinct cultivar was discovered and selected as a flowering plant within the progeny of the stated cross by Harry W. M. van Straalen in a controlled environment (greenhouse) in Rijsenhout, Holland in 1998. The first act of asexual reproduction of 'Dukaster' was accomplished when vegetative cuttings were taken from the initial selection in 1999 in a controlled environment in Rijsenhout, Holland.

SUMMARY OF THE INVENTION

The present invention is a new and distinct variety of Aster bearing medium sized blooms with pink ray-florets and yellow disc florets, which can be propagated by a cutting from a cutting and produced as pot plants in 8 weeks time.

BRIEF DESCRIPTION OF THE DRAWINGS

The present invention of a new and distinct variety of Aster is shown in the accompanying drawings, the color being as nearly true as possible with color photographs of this type.

Figure 1:
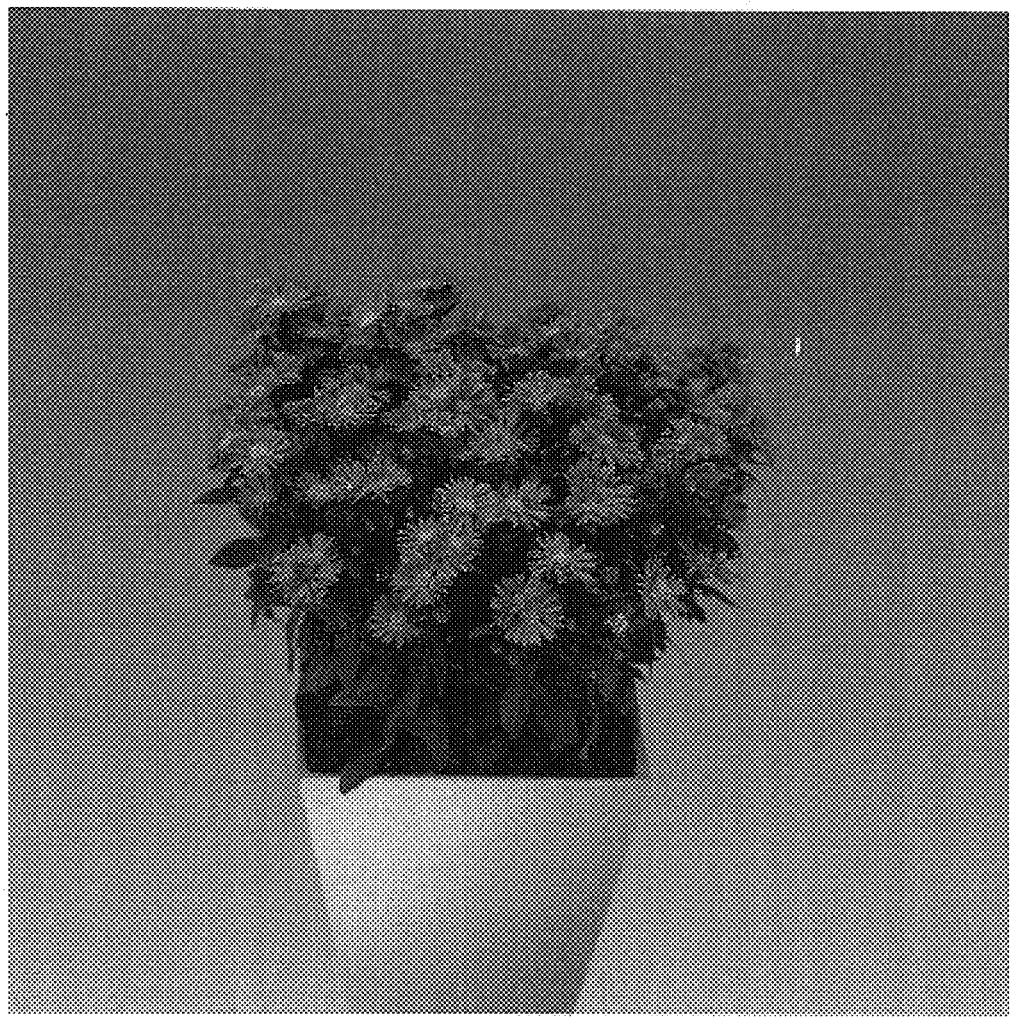
FIG. 1 shows a plant of the cultivar in full bloom.
Figure 2:
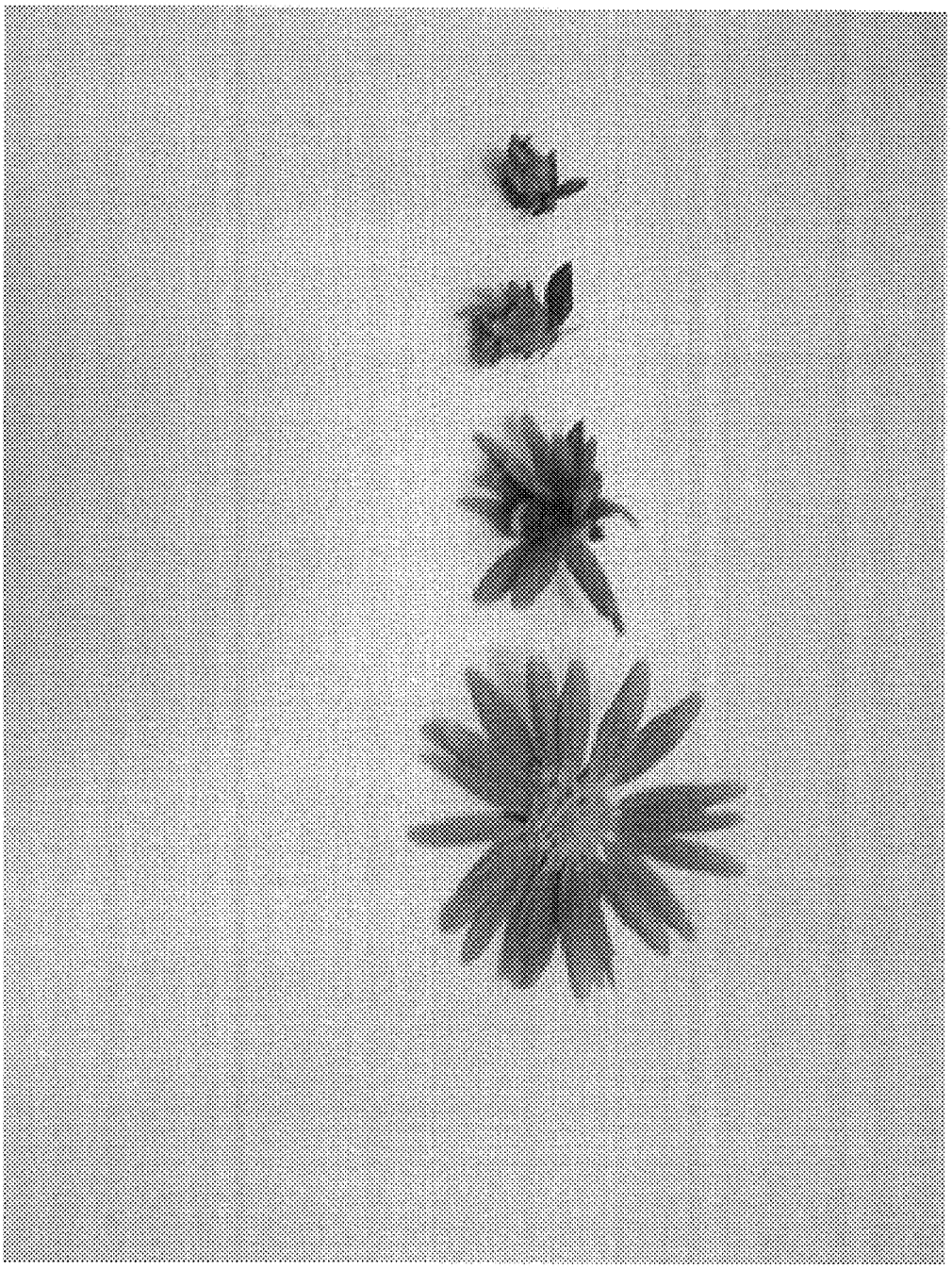
FIG. 2 shows the various stages of bloom of the new cultivar.
Figure 3:
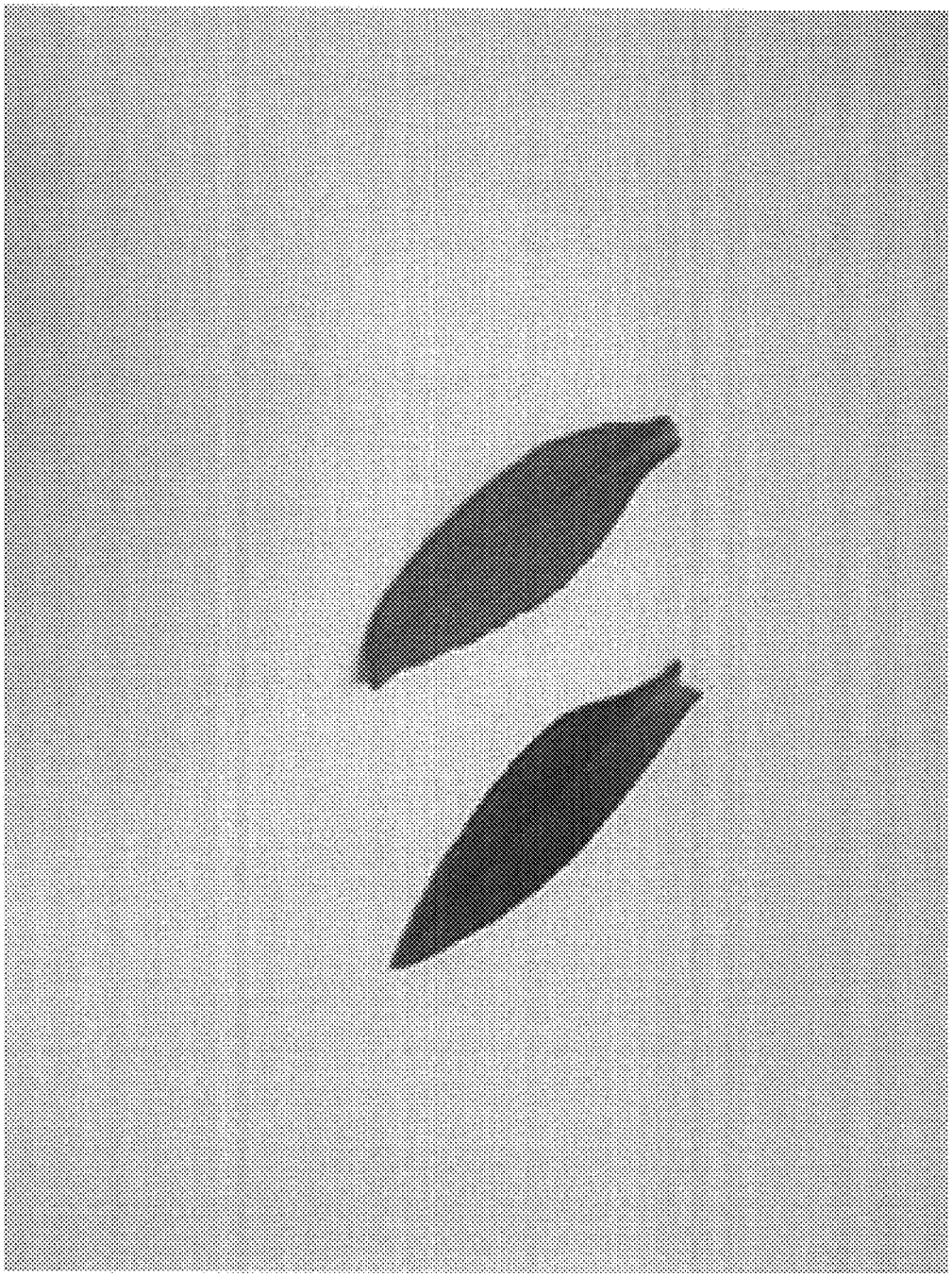
FIG. 3 shows the foliage of the new cultivar.

The figures are of a 9-week old plant, cultivated as further described in the rest of the application.

DESCRIPTION OF THE INVENTION

This new variety of Aster is of the botanical classification *Aster novi-belgii* L. The observations and measurements were gathered from plants grown in a greenhouse in Rijsenhout, Holland in a photo-periodic controlled crop under conditions generally used in commercial practice. The greenhouse temperatures during this crop were at day-time between 18° C. and 25° C. and at night 20° C. The photo-periodic response time in this crop was 39 days, after an average of 16 long days after sticking of the unrooted cuttings. Plants were pinched 10 days after sticking. Growth retardants were applied in an average dose of 1.5 gram/liter water, starting one week after pinching. The plants were observed (directly) during the flowering of this crop. The plant is susceptible to Powdery Mildew. No tests were done on cold or drought tolerance. This new variety produces medium sized blooms with pink ray-florets and yellow disc-florets blooming on the plant for 4 weeks. This new variety of Aster has been found to retain its distinctive characteristics throughout successive propagations; however, the phenotype may vary significantly with variations in environment such as light intensity and temperature. 'Dukaster' can be planted with assimilation lightning (high pressure sodium lamps) between week 5 and week 35 under greenhouse conditions in Holland.

From the cultivars known to the inventors the most similar existing cultivar in comparison to 'Dukaster' is 'Dynaster'. When 'Dynaster' and 'Dukaster' are being compared the following differences are noticed: The differences of 'Dynaster' and 'Dukaster' are (1) Flower color. (2) Anthocyanin coloration of stem. (1) The color of the ray-florets of 'Dynaster' is violet, while that of 'Dukaster' is pink. (2) In 'Dynaster' anthocyanin coloration is present in the stem, in 'Dukaster' no anthocyanin is present.

'Dukaster' differs from 'Diamaster' in (1) flowering response time, (2) flower size, and (3) ray-floret color. (1) The flowering response time of 'Diamaster' is 42 days, while the flowering response time of 'Dukaster' is 39 days. (2) The flower size of 'Diamaster' is small, while the flower size of 'Dukaster' is medium. (3) The 'Diamaster' ray-florets are white, while the 'Dukaster' ray-florets are pink.

The following is a description of the plant and characteristics that distinguish 'Dukaster' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of Cultivar 'Dukaster'

Bud:
- *Size.*—Medium; Cross-section 0.3 cm, height 0.5 cm.
- *Outside color.*—Red-purple 70 C.
- *Involucral bracts.*—2 rows, length 4 mm, width 3 mm.
- *Involucral bracts among disc-florets.*—Not present.
- *Involucral bracts color.*—Green 138 D.

Bloom:
- *Type.*—Daisy.
- *Size.*—Medium.
- *Fully expanded.*—3.5 cm.
- *Number of blooms per branch.*—11.
- *Peduncle length.*—3–3.5 cm.
- *Peduncle color.*—Green 139 B.
- *Peduncle angle.*—30°.
- *Performance on the plant.*—4 weeks.
- *Seeds.*—Produced in small quantities, oval/ovate shaped, grey-brown 199 A, 1 mm. in length.

Color:
- *Center of the bloom (disc-florets).*—Immature Yellow-green 151 A. Mature Yellow 1A.
- *Color of the ray-florets.*—Upper surface: Purple-violet 81 A. Lower surface: Violet 87 B.
- *Tonality from distance.*—A pot aster with pink flowers and a yellow disc.
- *Color of the upper surface of the ray-florets after aging of the plant.*—Purple-violet 81 A.

Ray florets:
- *Number of whorls of ray-florets.*—2.
- *Texture.*—Upper and under side smooth.
- *Number of ray-florets.*—20–22.
- *Shape in cross-section.*—Straight.
- *Curvature of longitudinal axis.*—Flat.
- *Length of corolla tube.*—0.4 cm.
- *Ray-floret length.*—2 cm.
- *Ray-floret width.*—0.2 cm.
- *Ratio length/width.*—10.
- *Shape of tip.*—Pointed.
- *Shape of apex.*—Acute.

Disc florets:
- *Disc diameter.*—0.9 cm.
- *Distribution of disc florets.*—Numerous, clearly visible at all stages of flowering.
- *Shape.*—Tubular.
- *Lenght.*—0.6 cm.
- *Color.*—Yellow-green 145 D.

Reproductive organs:
- *Stamen.*—Present in Disc florets only.
- *Stamen color.*—Yellow 13 A.
- *Pollen color.*—Yellow-orange 14 A.
- *Pollen.*—Very small amount.
- *Styles.*—Present in both Ray- and Disc-florets.
- *Style color.*—Yellow-green 150 D.
- *Style length.*—0.7 cm.
- *Ovaries.*—Enclosed in calyx.
- *Calyx shape.*—Pappus.
- *Calyx lenght.*—0.5 cm.
- *Calyx color.*—Yellow-green 150 D.

Plant:
- *Form.*—A pot aster meant for indoor use.
- *Growth habit.*—Upright growing.
- *Growth rate.*—Vigorous.
- *Height.*—25 cm.
- *Width.*—7.5 cm.
- *Internode lenght.*—2 cm.
- *Stem diameter.*—2–3 mm.
- *Stem color.*—Green 139 B.
- *Stem strength.*—Strong.
- *Stem brittleness.*—Not brittle.
- *Stem anthocyanin coloration.*—Absent.
- *Length of lateral branch.*—From top to bottom 20 cm.
- *Lateral branch color.*—Green 139 B.
- *Lateral branch, attachment.*—25°.
- *Branching (average number of lateral branches).*—Good with 3 breaks after pinching.
- *Internode length.*—0.2 cm.
- *Flowering response (photo-periodic controlled crop, not natural season).*—39 Days.

Foliage:
- *Leaf arrangement.*—Alternate.
- *Color immature stage.*—Upper side Yellow-green 144 A. Under side Yellow-green 146 C.
- *Color mature stage.*—Upper side Green 137 B. Under side Green 137 C.
- *Color midvein.*—Upper side Yellow-green 147 D. Under side Yellow-green 147 C.
- *Size.*—Medium; length 6 cm, width 2 cm.
- *Quantity (number per lateral branch).*—10.
- *Shape.*—Elliptic.
- *Texture upper side.*—Glabrous.
- *Texture under side.*—Glabrous.
- *Venation arrangement.*—Pinnately netted.
- *Shape of the margin.*—Sinuate.
- *Shape of base.*—Attenuate.
- *Apex.*—Acuminate.

Differences with the comparison varieties

| | 'Dukaster' | 'Dynaster' |
|---|---|---|
| Color ray-florets | Purple-violet 81 A | Violet-blue 90 D |
| Anthocyanin coloration in stem | Absent | Present |

I claim:

1. A new and distinct variety of Aster plant as described and illustrated.

* * * * *